US006258852B1

(12) United States Patent
Flitter et al.

(10) Patent No.: US 6,258,852 B1
(45) Date of Patent: Jul. 10, 2001

(54) ARYL NITRONE THERAPEUTICS FOR THE TREATMENT OF INFLAMMATORY BOWEL DISEASE

(75) Inventors: William D. Flitter, Mountain View; William A. Garland, Los Gatos, both of CA (US); Beverly Greenwood Van-Meerveld, Oklahoma City, OK (US); Ian Irwin, Palo Alto, CA (US)

(73) Assignee: Centaur Pharmaceuticals, Inc., Sunnyvale, CA (US)

( * ) Notice: Subject to any disclaimer, the term of this patent is extended or adjusted under 35 U.S.C. 154(b) by 0 days.

(21) Appl. No.: 09/567,049

(22) Filed: May 8, 2000

Related U.S. Application Data

(62) Division of application No. 09/313,269, filed on May 18, 1999, now Pat. No. 6,083,989.
(60) Provisional application No. 60/085,961, filed on May 19, 1998.

(51) Int. Cl.[7] ............................ A61K 31/15; A61K 31/44; A61K 31/405; C07C 303/00; C07C 233/00
(52) U.S. Cl. ............................ 514/640; 514/278; 514/415; 514/603; 514/630; 514/641; 564/86; 564/220; 564/275; 548/505
(58) Field of Search ................................... 514/640, 278, 514/415, 603, 641; 564/86, 220, 275; 548/505

(56) References Cited

U.S. PATENT DOCUMENTS

| 5,036,097 | | 7/1991 | Floyd et al. | 514/400 |
|---|---|---|---|---|
| 5,292,746 | | 3/1994 | Bernotas et al. | 514/278 |
| 5,622,994 | * | 4/1997 | Carney et al. | 514/643 |
| 6,046,232 | * | 4/2000 | Kelleher et al. | 514/464 |

FOREIGN PATENT DOCUMENTS

| 0 474 403 A1 | 11/1992 | (EP) . |
|---|---|---|
| 92/22290 | 12/1992 | (WO) . |
| 95/11227 | 4/1995 | (WO) . |
| 97/00680 | 1/1997 | (WO) . |
| 97/30990 | 8/1997 | (WO) . |
| 97/39751 | 10/1997 | (WO) . |
| 99/20601 | 4/1999 | (WO) . |

OTHER PUBLICATIONS

Anana, RD et al. (1997) Synthesis and smooth–muscle calcium–channel effects of dialkyl 1,4–dihydro–2,6–dimethy–4–aryl–3,5–pyridinedicarboxylates containing a nitrone moiety in the 4–aryl substituent, *Arch. Pharm. (Weinheim, Ger.)* 330: 53–58.
Bonner, GF (1996) Current medical therapy for inflammatory bowel disease, *Southern Medical Journal*, 89: 556–566.
Buettner, GR (1987) ESR Parameters of Spin Adducts, *Free Radical Biology*, 3: 259–303.

Calkins, BM, Mendeloff, Al (1986) Epidemiology of Inflammatory Bowel Disease, *Epidemiology Review* 8: 60–90.
Cao, X. and Phillis, JW (1994) a–Phenyl–N–tert–butyl–nitrone Reduces Cortical Infarct and Edema in Rats Subjected to Focal Ischemia. *Brain Res.* 644: 267–272.
Carney, JM. Starke–Reed, PE Oliver, CN, Landrum, RW, Cheng, MS, Wu, JF and Floyd, RA (1991) Reversal or age–related increase in brain protein oxidation in enzyme activity, and loss in temporal and spatial memory by chronic administration of the spin–trapping compound N–tert–butyl–α–phenylnitrone. *Proc. Natl. Acad. Sci.*, 88: 3633–3636.
Castro, GA, Roy, SA, Stockstill, RD (1974) Trichinella Spiralis: Peroxidase Activity in Isolated Cells from the Rat Intestine, *Exp. Parasitol.*, 36: 307–315.
Crotty, B. (1994) Ulcerative Colitis and Xenobiotic Metabolism, *Lancet*, 343:35–38.
Edamatsu,R, Mori,A., Packer, L (1995) The Spin Trap N–tert–α–phenyl–butylnitrone Prolongs the Life Span of the Senescence Accelerated Mouse, *Biochem Biophys Res Comm* 211: 847–849.
Elson, CO, Startor, RB, Tennyson, GS, Ridell, RH (1995), Experimental Models of Inflammatory Bowel Disease, *Gastroenterology*, 109: 1344–1367.
Floyd, RA and Carney, J., Nitrone Radical Traps (NRTs) Protect in Experimental Neurodegenerative Diseases, in *Neuroprotective Approaches to the Treatment of Parkinson's Disease and Other Neurodegenerative Disorders* (Olanow, CW, Jenner, P and Youssim E, Eds.) Academic Press, New York, New York, in press.
Glickman, RM (1994) Inflammatory Bowel Disease in *Harrison's Principles of Internal Medicine* (McGraw Hill, New York, NY) Chapter 255: 1403–1416.
Grisham MB, MacDermott, RP, Deitch EA (1990), Oxidant Defence Mechanisms in the Human Colon, *Inflammation*, 14: 669–680.
Hamburger, SA, McCay, PB (1989) Endotoxin–Induced Mortality in Rats is Reduced by Nitrones, *Circulatory Shock*, 29: 329–334.
Hanauer, SB, Baert, F. (1994) Medical Therapy of Inflammatory Bowel Disease, *Med Clin North Am*, 78: 1413–1426.
Hanauer, B. (1993) Medical Therapy of Ulcerative Colitis, *Lancet*, 342: 412–417.

(List continued on next page.)

Primary Examiner—Theodore J. Criares
Assistant Examiner—Jennifer Kim
(74) *Attorney, Agent, or Firm*—Burns, Doane, Swecker & Mathis, LLP

(57) ABSTRACT

Disclosed are methods for treating or preventing inflammatory bowel disease (IBD) using aryl nitrone compounds. Pharmaceutical compositions containing aryl nitrone compounds which are useful for the treatment or prophylaxis of IBD are also disclosed.

5 Claims, No Drawings

OTHER PUBLICATIONS

Harris, ML, Schiller, HJ, Reilly, PM, Donowitz, M, Grisham, MB, Bulkley (1992), Free Radicals and Other Reactive Oxygen Metabolites in Inflammatory Bowel Disease: Cause, Consequence or Epiphenomenom, *Pharmacol. Ther.*, 53: 375–408.

Higa, A. McKnight, GW, Wallace, JL (1993) Attenuation of Epithelial Injury in Acute Experimental Colitis by Immunomodulators, *Eur. J. Pharmacol.* 239: 171–178.

Levin, B. (1992) Inflammatory Bowel Disease and Colon Cancer, *Cancer* (Supplement), 70:1313–1316.

MacDermott, RP (1994) Alterations in the Mucosal System in Ulcerative Colitis and Crohn's Disease, *Med Clin North Am*, 78: 1207–1231.

McKechnie, K., Furman, BL, Paratt JR (1986), Modification by Oxygen Free Radical Scavengers of the Metabolic and Cardiovascular Effects of Endotoxin Infusion in Conscious Rats, *Circulatory Shock* 19: 429–439.

Miyajima, T., Kotake, Y. (1995) Spin Trapping Agent, Phenyl N–Tert_Butyl Nitrone, Inhibits Induction of Nitric Oxide Synthase in Endotoxin–Induced Shock in Mice, *Biochem Biophys Res Commun*, 215: 114–121.

Novelli, GP (1992) Oxygen Radicals in Experimental Shock: Effects of Spin–Trapping Nitrones in Ameliorating Shock Pathophysiology, *Critical Care Medicine*, 20: 499–507.

Oliver, CN, Starke–Reed, PE, Stadtman, ER, Carney, JM and Floyd, RA (1990) Oxidative Damage to Brain Proteins, Los of Glutamine Synthetase Activity and Production of Free radicals During Ischemia Induced Injury to Gerbil Brain. *Proc. Natl. Acad. Sci. USA* 87: 5144–5147.

Progrebniak, HW, Merino, MJ, Hahn, SM, Mitchell, JB, Pass, HI (1992) Spin Trap Salvage from Endotoxemia: The Role of Cytokine Down–Regulation, *Surgery*, 112: 130–139.

Thomas CE et al. (1996) Characterization of the radical trapping activity of a novel series of cyclic nitrone spin taps, *Journal of Biological Chemistry*, 271: 3097–3104.

Wallce, JA, MacNaughton, WK, Morris, GP, Beck PL (1989) Inhibition of Leulotriene Synthesis Markedly Accelerates Healing in a Rat Model of Inflammatory Bowel Disease, *Gastroenterology*, 95: 29–35.

Winrow, VR, Winyard, PG, Morris, CJ, Blake, DR (1993) Free Radicals in Inflammation: Second Messengers and Mediators of Tissue Destruction, *Br Med Bull* 49: 506–522.

Yamada, T, Marshall, S, Specian, RD, Grisham, MB (1992) A Comparative Analysis of Two Models of Colitis in Rats, *Gastroenterology*, 102: 1524–1534.

Zhao, Q., Pahlmark, K., Smith, M.–J., and Siesjo, B. (1994) DelayedTreatment with the Spin Trap a–phenyl–n–tert–butyl nitrone (PBN) Reduces Infarct Size Following Transient Middle Cerebral Artery Occlusion in Rats. *Acta Physiol. Scad.* 152: 349–350.

* cited by examiner

ARYL NITRONE THERAPEUTICS FOR THE TREATMENT OF INFLAMMATORY BOWEL DISEASE

CROSS-REFERENCE TO RELATED APPLICATIONS

This application is a divisional, of application Ser. No. 09/313,269, filed May 18, 1999, now U.S. Pat. No. 6,083,989.

This application claims the benefit of U.S. patent application Ser. No. 60/085,961, filed May 19, 1998, the disclosure of which is incorporated herein by reference in its entirety.

BACKGROUND OF THE INVENTION

1. Field of the Invention

This invention relates to the treatment of inflammatory bowel disease (IBD). More specifically, this invention is directed to methods for treating or preventing IBD using aryl nitrone compounds. This invention is also directed to pharmaceutical compositions containing aryl nitrone compounds which are useful for the treatment or prophylaxis of IBD.

2. State of the Art

The term inflammatory bowel disease ("IBD") describes a group of chronic inflammatory disorders of unknown causes involving the gastrointestinal tract ("GI tract"). The prevalence of IBD in the US is estimated to be about 200 per 100,000 population or approximately 500,000 people. Patients with IBD can be divided into two major groups, those with ulcerative colitis ("UC") and those with Crohn's disease ("CD").

In patients with UC, there is an inflammatory reaction primarily involving the colonic mucosa. The inflammation is typically uniform and continuous with no intervening areas of normal mucosa. Surface mucosal cells as well as crypt epithelium and submucosa are involved in an inflammatory reaction with neutrophil infiltration. Ultimately, this situation typically progresses to epithelial damage with loss of epithelial cells resulting in multiple ulcerations, fibrosis, dysplasia and longitudinal retraction of the colon.

CD differs from UC in that the inflammation extends through all layers of the intestinal wall and involves mesentery as well as lymph nodes. CD may affect any part of the alimentary canal from mouth to anus. The disease is often discontinuous, i.e., severely diseased segments of bowel are separated from apparently disease-free areas. In CD, the bowel wall also thickens which can lead to obstructions. In addition, fistulas and fissures are not uncommon.

Clinically, IBD is characterized by diverse manifestations often resulting in a chronic, unpredictable course. Bloody diarrhea and abdominal pain are often accompanied by fever and weight loss. Anemia is not uncommon, as is severe fatigue. Joint manifestations ranging from arthralgia to acute arthritis as well as abnormalities in liver function are commonly associated with IBD. Patients with IBD also have an increased risk of colon carcinomas compared to the general population. During acute "attacks" of IBD, work and other normal activity are usually impossible, and often a patient is hospitalized.

Although the cause of IBD remains unknown, several factors such as genetic, infectious and immunologic susceptibility have been implicated. IBD is much more common in Caucasians, especially those of Jewish descent. The chronic inflammatory nature of the condition has prompted an intense search for a possible infectious cause. Although agents have been found which stimulate acute inflammation, none has been found to cause the chronic inflammation associated with IBD. The hypothesis that IBD is an autoimmune disease is supported by the previously mentioned extraintestinal manifestation of IBD as joint arthritis, and the known positive response to IBD by treatment with therapeutic agents such as adrenal glucocorticoids, cyclosporine and azathioprine, which are known to suppress immune response. In addition, the GI tract, more than any other organ of the body, is continuously exposed to potential antigenic substances such as proteins from food, bacterial byproducts (LPS), etc.

Once the diagnosis has been made, typically by endoscopy, the goals of therapy are to induce and maintain a remission. The least toxic agents which patients are typically treated with are the aminosalicylates. Sulfasalazine (Azulfidine), typically administered four times a day, consists of an active molecule of aminosalicylate (5-ASA) which is linked by an azo bond to a sulfapyridine. Anaerobic bacteria in the colon split the azo bond to release active 5-ASA. However, at least 20% of patients cannot tolerate sulfapyridine because it is associated with significant side-effects such as reversible sperm abnormalities, dyspepsia or allergic reactions to the sulpha component. These side effects are reduced in patients taking olsalazine. However, neither sulfasalazine nor olsalazine are effective for the treatment of small bowel inflammation. Other formulations of 5-ASA have been developed which are released in the small intestine (e.g. mesalamine and asacol). Normally it takes 6–8 weeks for 5-ASA therapy to show full efficacy.

Patients who do not respond to 5-ASA therapy, or who have a more severe disease, are prescribed corticosteroids. However, this is a short term therapy and cannot be used as a maintenance therapy. Clinical remission is achieved with corticosteroids within 2–4 weeks, however the side effects are significant and include a Cushing goldface, facial hair, severe mood swings and sleeplessness. The response to sulfasalazine and 5-aminosalicylate preparations is poor in Crohn's disease, fair to mild in early ulcerative colitis and poor in severe ulcerative colitis. If these agents fail, powerful immunosuppressive agents such as cyclosporine, prednisone, 6-mercaptopurine or azathioprine (converted in the liver to 6-mercaptopurine) are typically tried. For Crohn's disease patients, the use of corticosteroids and other immunosuppressives must be carefully monitored because of the high risk of intra-abdominal sepsis originating in the fistulas and abscesses common in this disease. Approximately 25% of IBD patients will require surgery (colectomy) during the course of the disease.

Oxygen-derived free radicals such as HO., the superoxide anion and other reactive oxygen species such as HOCl, have emerged as a common pathway of tissue injury in a wide variety of diseases whose underlying cause is an inappropriately vigorous and sustained immune response (failure to control or down regulate response to the initial, appropriate stimulus). Examples of other diseases, in addition to IBD and arthritis, where this mechanism appear to be the operative cause are ARDS, septic shock, asthma, diabetes, multiple sclerosis, uveitis, etc. Typically, both a cytokine-mediated immune response and a nonspecific inflammatory cascade are involved in the primary inappropriate response with both responses mediated through active oxygen species (oxidative stress). The inappropriate secondary response, also mediated through oxidative stress) may involve tissue damaging oxidation by neutrophils and tissue macrophages.

Various approaches have been taken to suppress this inappropriate inflammatory response. Small molecule inhibitors of the various leukotriene, PAF and cyclooxygenase pathways have shown only limited efficacy, perhaps because blocking only one of many pathways does not provide a sufficiently large decrease in overall oxidative stress. Another approach has been the use of antibodies or cloned receptor molecules which target specific proteins in the inflammatory cascade such as IL-1, IL-6 or TNF-α. However, this approach is practical only for acute conditions, like septic shock or ARDS, where IV administration and antibody formation against the therapeutic protein is less of a concern. For a chronic condition like IBD, an orally active small molecule that is fully active when dosed once-a-day would be the preferred method of treatment.

Another approach to mitigating the oxidative stress resulting from an inflammatory response is to employ nitrone-related therapeutics (NRTs). The prototype NRT is α-phenyl-t-butyl nitrone (PBN) shown below.

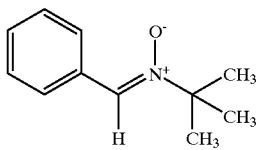

NRTs represent a new category of therapeutics with the inherent capacity to overcome the shortcomings of other previously studied compounds. Among other properties, NRTs such as PBN are believed to trap free radicals (R.) by adding the radical to form a more unreactive nitroxyl free radical.

Nitrones were first used as analytical tools capable of reacting with highly reactive radicals to yield free radical adducts that are much less reactive. In many cases, the free radical/nitrone adduct complex is stable enough to allow in vivo isolation and quantitation using electron spin resonance (ESR). The concept of using nitrones as therapeutics in, for example, neurodegenerative diseases resulted from the observations that nitrones, such as PBN, trap reactive oxygen species and/or secondary free radicals following ischemia. The therapeutic effects of nitrones may result because the nitrones convert highly reactive radicals into much less reactive products. Certain NRTs have been shown to protect experimental animals from ischemia/reperfusion injury (stroke). NRTs, administered chronically, reverse the age-associated increase in oxidatively damaged protein and the age-associated decrease in the activity of the oxidative-sensitive enzyme, glutamine synthetase, in the brain.

Accompanying the NRT-mediated changes in oxidized protein and glutamine synthetase activity is a significant improvement in the performance of animals in behavioral tests measuring short-term spatial memory. For example, it has been shown that prototype NRTs mitigate the effects of this inflammatory cascade in a number of in vivo models. Of particular interest is the consistent and well documented protection shown by PBN against the lethality induced by LPS in various rodent models of septic shock. Remarkably, PBN has also been shown to increase the life span of senescence-accelerated mice by one third, perhaps by mitigating free radical damage. PBN has also been shown to block inducible nitric oxide synthetase ("iNOS"), the enzyme responsible for producing large amounts of the highly damaging NO. Thus, PBN can both trap HO. and suppress formation of NO., potentially neutralizing the effects of the two agents considered to be the most damaging to tissue.

When evaluating the prospects of using an antioxidant to successfully treat IBD, it is perhaps also useful to consider that the anti-oxidant defense of the human colon is relatively deficient compared to human liver (mucosal levels of SOD, catalase and GSH representing 8%, 4% and 40%, respectively of liver levels), thus leaving the colon particularly sensitive to oxidative stress. A considerable number of chemical modifications have been made to increase NRTs suitability as therapeutic agents. The effects of intrinsic chemical reactivity and radical trapping ability have been examined by substituting the phenyl ring with electron donating or electron withdrawing substituents. More water soluble analogues have also been made which, for example, have a carboxylate or sodium sulfonate group on the phenyl ring. In addition, lipophilic analogues have been made with functional group substitutions on either the phenyl ring or the nitronyl nitrogen. The alkyl nitrogen substituent has also been varied through the standard straight chain and branched $C_3$–$C_5$ substituents. Nitrone isosteres and related compounds have also targeted and examined for efficacy. This approach has led to various classes of compounds, such as substituted ureas, amides, thioamides, azoxy derivatives, sulphones, and hydroxamic acids. Among these, some benzamide compounds substantially similar in structure to some nitrones, such as PBN, have been shown to have activity in the treatment of Parkinson's disease, HIV dementia, and related conditions.

As a final aspect of background, in evaluating the effectiveness of compounds in the treatment of IBD, an in vivo model based upon trinitrobenzene sulfonic acid ("TNBS") is used.

References relating to the above-mentioned subjects include:

Glickman, R M (1994) Inflammatory Bowel Disease in *Harrison's Principles of Internal Medicine* (McGraw Hill, New York, N.Y.) Chapter 255: 1403–1416.

Calkins, B M, Mendeloff, A l (1986) Epidemiology of Inflammatory Bowel Disease, *Epidemiology Review* 8: 60–90.

Levin, B. (1992) Inflammatory Bowel Disease and Colon Cancer, *Cancer (Supplement)*, 70: 1313–1316.

Crotty, B. (1994) Ulcerative Colitis and Xenobiotic Metabolism, *Lancet,* 343: 35–38.

Hanauer, S B, Baert, F. (1994) Medical Therapy of Inflammatory Bowel Disease, *Med Clin North Am,* 78: 1413–1426.

MacDermott, R P (1994) Alterations in the Mucosal System in Ulcerative Colitis and Crohn's Disease, *Med Clin North Am,* 78: 1207–1231.

Hanauer, B. (1993) Medical Therapy of Ulcerative Colitis, *Lancet,* 342: 412–417.

Winrow, V R, Winyard, P G, Morris, C J, Blake, D R (1993) Free radicals in Inflammation: Second Messengers and Mediators of Tissue Destruction, *Br Med Bull* 49: 506–522.

Floyd, R A and Carney, J., Nitrone Radical Traps (NRTs) Protect in Experimental Neurodegenerative Diseases, in *Neuroprotective Approaches to the Treatment of Parkinson's Disease and Other Neurodegenerative Disorders* (Olanow, C W, Jenner, P and Youssim E, Eds.) Academic Press, New York, N.Y., in press.

Cao, X. and Phillis, J W (1994) a-Phenyl-N-tert-butylnitrone Reduces Cortical Infarct and Edema in Rats Subjected to Focal Ischemia. *Brain Res.* 644: 267–272.

Zhao, Q., Pahlmark, K., Smith, M.-J., and Siesjo, B. (1994) Delayed Treatment with the Spin Trap a-phenyln-tert-butyl nitrone (PBN) Reduces Infarct Size Following Transient Middle Cerebral Artery Occlusion in Rats. *Acta Physiol. Scad.* 152: 349–350.

Oliver, C N, Starke-Reed, P E, Stadtman, E R, Carney, J M and Floyd, R A (1990) Oxidative Damage to Brain Proteins, Los of Glutamine Synthetase Activity and Production of Free Radicals During Ischemia Induced Injury to Gerbil Brain. *Proc. Natl. Acad. Sci.* USA 87: 5144–5147.

Carney, J M, Starke-Reed, P E Oliver, C N, Landrum, R W, Cheng, M S, Wu, J F and Floyd, R A (1991) Reversal or age-related increase in brain protein oxidation in enzyme activity, and loss in temporal and spatial memory by chronic administration of the spin-trapping compound N-tert-butyl-α-phenylnitrone. *Proc. Natl. Acad. Sci.,* 88: 3633–3636.

Novelli, G P (1992) Oxygen Radicals in Experimental Shock: Effects of Spin-Trapping Nitrones in Ameliorating Shock Pathophysiology, *Critical Care Medicine*, 20: 499–507.

Hamburger, S A, McCay, P B (1989) Endotoxin-Induced Mortality in Rats is Reduced by Nitrones, *Circulatory Shock,* 29: 329–334.

Progrebniak, H W, Merino, M J, Hahn, S M, Mitchell, J B, Pass, H I (1992) Spin Trap Salvage from Endotoxemia: The Role of Cytokine Down-Regulation, *Surgery,* 112: 130–139.

McKechnie, K., Furman, B L, Paratt J R (1986), Modification by Oxygen Free Radical Scavengers of the Metabolic and Cardiovascular Effects of Endotoxin Infusion in Conscious Rats, *Circulatory Shock* 19: 429–439.

Edamatsu,R, Mori,A., Packer, L (1995) The Spin Trap N-tert-α-phenyl-butylnitrone Prolongs the Life Span of the Senescence Accelerated Mouse, *Biochem Biophys Res Comm* 211: 847–849.

Miyajima, T., Kotake, Y. (1995) Spin Trapping Agent, Phenyl N-Tert_Butyl Nitrone, Inhibits Induction of Nitric Oxide Synthase in Endotoxin-Induced Shock in Mice, *Biochem Biophys Res Commun,* 215: 114–121.

Boettner, G R (1987) ESR Parameters of Spin Adducts, *Free Radical Biology,* 3: 259–303.

Harris, M L, Schiller, H J, Reilly, P M, Donowitz, M, Grisham, M B, Bulkley (1992), Free Radicals and Other Reactive Oxygen Metabolites in Imflammatory Bowel Disease: Cause, Consequence or Epiphenomenom, *Pharmacol. Ther.,* 53: 375–408.

Grisham M B, MacDermott, R P, Deitch E A (1990), Oxidant Defence Mechanisms in the Human Colon, *Inflammation,* 14: 669–680.

Elson, C O, Startor, R B, Tennyson, G S, Ridell, R H (1995), Experimental Models of Inflammatory Bowel Disease, *Gastroenterology,* 109: 1344–1367.

Yamada, T, Marshall, S, Specian, R D, Grisham, M B (1992) A Comparative Analysis of Two Models of Colitis in Rats, *Gastroenterology,* 102: 1524–1534.

Wallace, J A, MacNaughton, W K, Morris, G P, Beck P L (1989) Inhibition of Leulotriene Synthesis Markedly Accelerates Healing in a Rat Model of Inflammatory Bowel Disease, *Gastroenterology,* 95: 29–35.

Higa, A. McKnight, G W, Wallace, J L (1993) Attenuation of Epithelial Injury in Acute Experimental Colitis by Immunomodulators, *Eur. J. Pharmacol.* 239: 171–178.

Castro, G A, Roy, S A, Stockstill, R D (1974) Trichinella Spiralis: Peroxidase Activity in Isolated Cells from the Rat Intestine, *Exp. Parasitol.,* 36: 307–315.

SUMMARY OF THE INVENTION

It has now been found that certain aryl nitrone compounds are effective for the treatment and prophylaxis of IBD.

Accordingly, in one of its composition aspects, this invention provides a pharmaceutical composition for the treatment or prophylaxis of inflammatory bowel disease comprising a pharmaceutically acceptable carrier and an effective inflammatory bowel disease-treating amount of a compound selected from the group consisting of:

N-cyclohexyl-α-(2-ethoxyphenyl)nitrone,

N-tert-butyl-α-(3,5-di-tert-butyl-2-hydroxyphenyl) nitrone,

N-isobutyl-α-phenylnitrone,

N-tert-butyl-α-(4-benzyloxyphenyl)nitrone,

N-cyclobutyl-α-(2-ethoxyphenyl)nitrone,

N-benzyl-α-(4-acetamidophenyl)nitrone,

N-cyclopentyl-α-(2-ethoxyphenyl)nitrone,

N-tert-butyl-α-(1-methylindol-3-yl)nitrone,

N-tert-butyl-α-(3,5-di-tert-butyl-4-acetoxy)nitrone, spiro[cyclohexane-1,3']-6-methoxy-3,4-dihydroisoquinoline-N-oxide, N-tert-butyl-α-(4-aminosulfonylphenyl)nitrone, and pharmaceutically acceptable salts thereof.

Another aspect of this invention is directed to methods for treating a patient suffering from or susceptible to an inflammatory bowel condition. Accordingly, this invention provides a method for treating a patient suffering from or susceptible to an inflammatory bowel condition comprising administering to said patient a pharmaceutical composition comprising a pharmaceutically acceptable carrier and an effective inflammatory bowel condition-treating amount of a compound selected from the group consisting of:

N-cyclohexyl-α-(2-ethoxyphenyl)nitrone,

N-tert-butyl-α-(3,5-di-tert-butyl-2-hydroxyphenyl) nitrone,

N-isobutyl-α-phenylnitrone,

N-tert-butyl-α-(4-benzyloxyphenyl)nitrone,

N-cyclobutyl-α-(2-ethoxyphenyl)nitrone,

N-benzyl-α-(4-acetamidophenyl)nitrone,

N-cyclopentyl-α-(2-ethoxyphenyl)nitrone,

N-tert-butyl-α-(1-methylindol-3-yl)nitrone,

N-tert-butyl-α-(3,5-di-tert-butyl-4-acetoxy)nitrone, spiro[cyclohexane-1,3']-6-methoxy-3,4-dihydroisoquinoline-N-oxide, N-tert-butyl-α-(4-aminosulfonylphenyl)nitrone, and pharmaceutically acceptable salts thereof.

In another of its method aspects, this invention provides a method for treating or preventing inflammatory bowel disease comprising:

(a) identifying a patient suffering from or susceptible to an inflammatory bowel condition; and (b) administering to said patient a pharmaceutical composition comprising a pharmaceutically acceptable carrier and an effective inflammatory bowel condition-treating amount of a compound selected from the group consisting of:

N-cyclohexyl-α-(2-ethoxyphenyl)nitrone,

N-tert-butyl-α-(3,5-di-tert-butyl -2-hydroxyphenyl) nitrone,

N-isobutyl-α-phenylnitrone,

N-tert-butyl-α-(4-benzyloxyphenyl)nitrone,

N-cyclobutyl-α-(2-ethoxyphenyl)nitrone,
N-benzyl-α-(4-acetamidophenyl)nitrone,
N-cyclopentyl-α-(2-ethoxyphenyl)nitrone,
N-tert-butyl-α-(1-methylindol-3-yl)nitrone,
N-tert-butyl-α-(3,5-di-tert-butyl-4-acetoxy)nitrone,
spiro[cyclohexane-1,3']-6-methoxy-3,4-dihydroisoquinoline-N-oxide,
N-tert-butyl-α-(4-aminosulfonylphenyl)nitrone,
and pharmaceutically acceptable salts thereof.

In the methods of this invention, the pharmaceutical compositions may be administered orally, parenterally, or rectally. The methods of this invention are be effective where the inflammatory bowel condition is ulcerative colitis or Crohn's disease.

In one embodiment of the above methods, the pharmaceutical composition is preferably administered as an oral dose in an amount of from 0.1 to about 150 mg/kg of patient weight.

In another embodiment of the above methods, the pharmaceutical composition is preferably administered intravenously in an amount of from about 0.01 mg/kg/hour to about 100 mg/kg/hour of patient weight for at least about 1 hour.

In still another embodiment of the above methods, the pharmaceutical composition is preferably administered rectally in an amount of from 1 to about 150 mg/kg of patient weight.

In one of its composition aspects, this invention is also directed to novel aryl nitrone compounds. Accordingly, this invention is directed to each of the following compounds:
N-isobutyl-α-phenylnitrone,
N-cyclobutyl-α-(2-ethoxyphenyl)nitrone,
N-benzyl-α-(4-acetamidophenyl)nitrone,
N-tert-butyl-α-(1-methylindol-3-yl) nitrone,
N-tert-butyl-α-(4-aminosulfonylphenyl)nitrone,
and pharmaceutically acceptable salts thereof.

DETAILED DESCRIPTION OF THE INVENTION

The treatment methods and pharmaceutical compositions of this invention employ one or more aryl nitrones as the active agent. For the purposes of this invention, the aryl nitrone compounds are named using conventional nitrone nomenclature, i.e., the carbon atom of the carbon-nitrogen double bond (C=N) is designated the a-position and substituents on the nitrogen atom of the carbon-nitrogen double bond are given the N- prefix. For example, N-tert-butyl-α-(4-benzyloxyphenyl)nitrone has the formula:

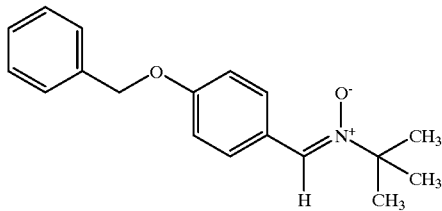

All geometric isomers of the nitrone compounds of formula I are included within the scope of this invention including, for example, all isomers (i.e., E and Z isomers) of the carbon-nitrogen double bond of the nitrone functionality. Cyclic nitrones are named using the nomenclature of U.S. Pat. No. 5,292,746, issued Mar. 8, 1994 to Carr, the disclosure of which is incorporated herein by reference in its entirety.

Definitions

When describing the aryl nitrones, pharmaceutical compositions and methods of this invention, the following terms have the following meanings unless otherwise specified.

"Acetamido" refers to the group "—NHC(O)CH$_3$".

"Aminosulfonyl" refers to the group "—S(O)$_2$NH$_2$".

"1-Hydroxy-2-methylprop-2-yl" refers to the group "—C(CH$_3$)$_2$CH$_2$OH".

"Sulfonate" or "sulfo" refers to the group "—SO$_3$H" and salts thereof.

"Pharmaceutically acceptable salt" refers to salts which are acceptable for administration to mammals including, by way of illustration, alkali and alkaline earth metal salts and addition salts of free acids and amines. Such pharmaceutically acceptable salts may be derived from a variety of organic and inorganic counter-ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "pharmaceutically acceptable cation" refers to a pharmaceutically acceptable cationic counterion of an acidic functional group. Such cations are exemplified by sodium, potassium, calcium, magnesium, ammonium, tetraalkylammonium cations, and the like.

General Synthetic Procedures

The aryl nitrone compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protecting and deprotecting various functional groups are well known in the art. For example, numerous protecting groups, and their introduction and removal, are described in T. W. Greene and G. M. Wuts, *Protecting Groups in Organic Synthesis*, Second Edition, Wiley, N.Y., 1991, and references cited therein.

In a preferred method of synthesis, the aryl nitrone compounds of this invention are prepared by coupling benzaldehyde or a benzaldehyde derivative, such as 2,4-disulfobenzaldehyde, 4-acetamidobenzaldehyde or 4-aminosulfonylbenzaldehdye with a hydroxylamine of the formula:

HO—NH—R

wherein R$^1$ is isobutyl, tert-butyl, benzyl, 1-hydroxy-2-methylprop-2-ylamine under conventional reaction conditions.

The coupling reaction is typically conducted by contacting the benzaldehyde derivative with at least one equivalent, preferably about 1.1 to about 2 equivalents, of the hydroxylamine in an inert polar solvent such as methanol, ethanol, 1,4-dioxane, tetrahydrofuran, dimethylsulfoxide, dimethylformamide and the like. This reaction is preferably conducted at a temperature of from about 0° C. to about 100° C.

for about 1 to about 48 hours. Optionally, a catalytic amount of an acid, such as acetic acid, hydrochloric acid, p-toluenesulfonic acid and the like, may be employed in this reaction.

Additionally, when conducting the coupling reaction with 2,4-disulfobenzaldehyde, the sulfonate groups are preferably converted into suitable salts, such as the lithium, sodium or potassium salt, prior to contacting the hydroxylamine with the benzaldehyde compound. The sulfonate groups are readily converted into the corresponding salt by contacting the disulfonate with at least two equivalents of a suitable base, such as lithium hydroxide, sodium hydroxide, potassium hydroxide, sodium hydride and the like.

Upon completion of the coupling reaction, the aryl nitrone is recovered by conventional methods including precipitation, chromatography, filtration, distillation and the like.

The benzaldehyde compounds employed in the coupling reaction are commercially available or can be prepared from commercially available starting materials using conventional procedures and reagents.

The hydroxylamine compounds used in the coupling reaction are also known compounds or compounds which can be prepared from known compounds using conventional procedures and reagents. Typically, the hydroxylamine compounds are prepared by reducing the corresponding nitro compound (i.e., $R^1$—$NO_2$) using a suitable catalyst such as an activated zinc/acetic acid catalyst, activated zinc/ammonium chloride c r an aluminum/mercury amalgam catalyst. This reaction is typically conducted at a temperature ranging from about 15° C. to about 100° C. for about 0.5 to 12 hours, preferably about 2 to 6 hours, in an aqueous reaction media, such as an alcohol/water mixture in the case of the zinc catalyst or an ether/water mixture in the case of the aluminum amalgam catalyst. Aliphatic nitro compounds (in the form of their salts) can also be reduced to hydroxylamines using borane in tetrahydrofuran.

Since some hydroxylamines have limited stability, such compounds are generally prepared immediately prior to reaction with the benzaldehyde compound. Alternatively, hydroxylamines can often be stored (or purchased commercially) as their hydrochloride salts. In such cases, the free hydroxylamine is typically generated immediately prior to reaction with the benzaldehyde compound by reaction of the hydrochloride salt with a suitable base, such as sodium hydroxide, sodium methoxide and the like.

Alternatively, the aryl nitrones of this invention can be prepared by coupling the benzaldehyde compound with the appropriate amine to form an intermediate imine, then oxidizing the imine as described, for example, in Hinton et al., *J. Org. Chem.*, 1992, 57, 2646.

Additionally, the synthesis of N-tert-butyl-α-(2,4-disulfophenyl)nitrone is described in U.S. Pat. No. 5,475,032, issued Dec. 12, 1995 to J. M. Carney, the disclosure of which is incorporated herein by reference in its entirety.

The synthesis of cyclic nitrones is described, for example, in U.S. Pat. No. 5,292,746, issued Mar. 8, 1994 to Carr, the disclosure of which is incorporated herein by reference in its entirely.

Pharmaceutical Compositions

When used as pharmaceuticals, the aryl nitrones employed in this invention are typically administered in the form of a pharmaceutical composition. Such compositions can be prepared using procedures well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The aryl nitrone compound(s) is typically formulated into a pharmaceutical composition suitable for oral, parenteral (e.g. intravenous or intramuscular injection), or rectal (e.g. suppository) administration.

The compositions for oral administration can take the form of liquid solutions or suspensions, powders, tablets, capsules or the like. In such compositions, the aryl nitrone is usually a minor component (0.1 to about 50% by weight) with the remainder being various vehicles or carriers and processing aids helpful for forming the desired dosing form. A liquid form may include a suitable aqueous or nonaqueous vehicle with buffers, suspending dispensing agents, colorants, flavors and the like.

A solid form may include, for example, any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, sugar, methyl salicylate, or orange flavoring.

Injectable compositions are commonly based upon injectable sterile saline or phosphate-buffered saline or other injectable carriers known in the art. Again, the active aryl nitrone is typically a minor component, often being from about 0.05 to 10% by weight, with the remainder being the injectable carrier and the like.

Rectal administration is usually by suppository. Suppositories are generally made with a base component of cocoa butter, glycerinated gelatin, hydrogenated vegetable oils, mixtures of polyethylene glycols of various molecular weights, or fatty acid esters of polyethylene glycol. The active aryl nitrone is usually a minor component, often from about 0.05 to 20% by weight, with the remainder being the base component.

The components for orally administrable, injectable compositions and suppositories are merely representative. Other materials as well as processing techniques and the like are set forth in Part 8 of *Remington's Pharmaceutical Sciences*, 18th edition, 1990, Mack Publishing Company, Easton, Pa., 18042, which is incorporated herein by reference.

One can also administer the compounds of the invention in sustained release forms or from sustained release drug delivery systems. A description of representative sustained release materials can be found in the incorporated materials in *Remington's Pharmaceutical Sciences*.

Conditions Treated and Treatment Regimens

The conditions treated with the aryl nitrone-containing pharmaceutical compositions of this invention generally include IBD and the various symptoms which fall within a definition of IBD. The aryl nitrone-containing formulations are administered to achieve a therapeutic effect. For those aryl nitrone compounds that exhibit a long residency in the body, a once-a-day regimen is possible. Alternatively, multiple doses, such as up to three doses per day, typically, may offer more effective therapy. Thus, a single dose or a multidose regimen may be used.

In any event, the aryl nitrone-containing pharmaceutical composition is administered in such a manner so that compound is delivered into the patient's bloodstream. One excellent mode for accomplishing this is intravenous administration. Intravenous dose levels for treating IBD range from about 0.01 mg/kg/hour of active aryl nitrone to about 100 mg/kg/hour, all for from about 1 to about 120 hours and especially 1 to 96 hours. A preloading bolus of from about 50 to about 5000 mg may also be administered to achieve adequate steady state levels. Other forms of parenteral administration, such as intramuscular injection can be used, as well. In this case, similar dose levels are employed.

With oral dosing, one to three oral doses per day, each from about 0.1 to about 150 mg/kg of active aryl nitrone are employed, with preferred doses being from about 0.15 to about 100 mg/kg.

With rectal dosing, one to three rectal doses per day, each from about 1 to about 150 mg/kg of active aryl nitrone are employed, with preferred doses being from about 1 to about 100 mg/kg.

In any treatment regimen, the health care professional should assess the patient's condition and determine whether or not the patient would benefit from aryl nitrone treatment. Some degree of routine dose optimization may be required to determine an optimal doing level and pattern.

A positive dose-response relationship has been observed. As such and bearing in mind the severity of the side effects and the advantages of providing maximum possible amelioration of symptoms, it may be desired in some settings to administer large amounts of aryl nitrone, such as those described above.

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240–270 mg tablets (80–90 mg of active nitrone compound per tablet) in a tablet press.

Formulation 2—Capsules

A compound of formula I is admixed as a dry powder with a starch diluent in an approximate 1:1 weight ratio. The mixture is filled into 250 mg capsules 125 mg of active nitrone compound per capsule).

Formulation 3—Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Injection

The compound of formula I is dissolved in a buffered sterile saline injectable aqueous medium to a concentration of approximately 5 mg/mL.

The following synthetic and biological examples are offered to illustrate this invention and are not to be construed in any way as limiting the scope of this invention.

EXAMPLES

In the examples below, all temperatures are in degrees Celsius (unless otherwise indicated). Example A–C describe the synthesis of intermediates useful for preparing nitrones of this invention; Examples 1–8 describe the synthesis of various aryl nitrones; and the Bioassay Examples describe the testing of such compounds.

In the examples below, the following abbreviations have the following meanings. Abbreviations not defined below have their generally accepted meaning.

| | | |
|---|---|---|
| bd | = | broad doublet |
| bs | = | broad singlet |
| d | = | doublet |
| dd | = | doublet of doublets |
| dec | = | decomposed |
| dH$_2$O | = | distilled water |
| EtOAc | = | ethyl acetate |
| EtOH | = | ethanol |
| g | = | grams |
| h | = | hours |
| Hz | = | hertz |
| L | = | liter |
| m | = | multiplet |
| min | = | minutes |
| M | = | molar |
| MeOH | = | methanol |
| mg | = | milligram |
| MHz | = | megahertz |
| mL | = | milliliter |
| mmol | = | millimole |
| m.p. | = | melting point |
| N | = | normal |
| q | = | quartet |
| quint. | = | quintet |
| s | = | singlet |
| t | = | triplet |
| THF | = | tetrahydrofuran |
| tlc | = | thin layer chromatography |
| µg | = | microgram |
| µL | = | microliter |
| UV | = | ultraviolet |

Example A

Synthesis of N-tert-Butylhydroxylamine

Zinc dust (648 g) was added in portions to a cooled mixture of 2-methyl-2-nitropropane (503 g) and ammonium chloride (207 g) in deionized water (6 L) at such a rate so as to maintain the temperature below 18° C. The reaction mixture was stirred mechanically for 15 hours and then filtered. The solid was washed with hot water (1.75 L). The combined filtrate was saturated with potassium carbonate (4.6 Kg) and extracted with ethyl acetate (2×1300 mL). The organic solution was dried over anhydrous sodium sulfate, filtered and rotary evaporated to give the title compound (329 g, 75.7% yield) as white crystals. This material was used without further purification.

Spectroscopic data were as follows:

$^1$H NMR (CDCl$_3$, 270 MHz)δ=1.090 (s, 3 CH$_3$).

Example B

Synthesis of N-Isopropylhydroxylamine

Using the procedure of Example A above and 1-methyl-1-nitroethane, the title compound was prepared. The crude hydroxylamine product was used without further purification.

Example C

Synthesis of N-Cyclohexylhydroxylamine

Using the procedure of Example A above and 1-nitrocyclohexane, the title compound can be prepared. Alternatively, N-cyclohexylhydroxylamine hydrochloride may be purchased commercially from Aldrich Chemical Company, Inc., Milwaukee, Wis. USA and neutralized with a base, such as potassium carbonate, to provide the title compound.

Example 1

Synthesis of α-(4-Ethoxyphenyl)-N-cyclohexylnitrone

A solution of 4-ethoxybenzaldehyde (6.62 g, 44.1 mmol) in 200 mL of benzene was refluxed with N-cyclohexylhydroxylamine (6.61 g, 57.4 mmol) in the presence of p-toluenesulfonic acid (0.8 g, 4 mmol) for 72 h. After rotary evaporation, the residue was purified by recrystallization from hexanes and ethylene glycol dimethyl ether (100 mL, 3:1, v:v) to give the title compound (9.2 g, 84% yield) as a solid, m.p. 124.0° C.

Spectroscopic data were as follows:

IR (KBr, cm$^{-1}$): 2933.0, 2862 (CH), 1599.6 (C=N), 1297.0 (C—O—C) and 1149.4 (N—O).

$^1$H NMR (CDCl$_3$, 279 MHz): δ=8.20 (2H, d, J=8.9 Hz, phenyl 2H), 7.32 (1 H, s, nitronyl H), 6.88 (2H, d, J=8.9 Hz, phenyl 2H), 4.05 (2H, quartet, J=7.0 Hz, CH$_2$), 3.75 (1H, m, CH), 1.94 (6H, m, 6 CH), 1.68 (2H, m, 2 CH), 1.39 (2H, t, J=7.0 Hz, CH$_3$) and 1.27 (2H, m, 2 CH).

$^{13}$C NMR (CDCl$_3$, 67.9 MHz): δ=160.6, 132.1, 130.7, 123.8, 114.4, 75.0, 63.4, 30.8, 24.7 and 14.3.

Example 2

Synthesis of α-(3,5-Di-tert-butyl-2-hydroxyphenyl)-N-tert-butyinitrone

To a solution of tert-butylhydroxylamine (14.98 g, 168.4 mmol) in MeOH (160 mL) was added 2-hydroxybenzaldehyde (129.5 mmol) and 3 drops of 37% hydrochloric acid. The resulting solution was refluxed through a Soxhlet apparatus containing molecular sieves (40 g) until no more aldehyde was detected by TLC. The solvent was removed in vacuo and the residue was recrystallized from EtOAc. The title compound was isolated in 82.1% yield as a crystalline solid, m.p. 234.7–235.2° C. (R$_f$=0.66 on a silica gel plate using 1:4 EtOAc/hexanes as an eluant).

Spectroscopic data were as follows:

IR (KBr, cm$^{-1}$): 2955 (CH), 1586 (C=N), 1269 (N—O) and 1023 (C—O).

$^1$H NMR (CDCl$_3$, 270 MHz) δ=11.83 (1H, s, phenolic OH), 7.80 (1H, s, nitronyl H), 7.47 (1H, d, J=2.23 Hz, phenyl H), 6.92 (1H, d, J=2.23 Hz, phenyl H), 1.64 (9H, s, 3 CH$_3$), 1.45 (9H, s, 3 CH$_3$) and 1.29 (9H, s, 3 CH$_3$).

$^{13}$C NMR (CDCl$_3$, 270 MHz): δ=156.60, 141.10, 139.97, 138.45, 128.32, 26.11, 117.53, 69.70, 35.07, 33.85, 31.14, 29.34 and 28.07.

Example 3

Synthesis of N-Isobutyl-α-phenyinitrone

Isobutylamine (14.6 g, 0.2 mol) was cooled in an ice bath and benzaldehyde (10.6 g, 0.1 mol) was added dropwise, followed by addition of NaOH pellets with stirring. The reaction was then allowed to warm to room temperature and was stirred for 1 hour. TLC showed 100% conversion of benzaldehyde. The reaction mixture was mixed with 60 mL of dichloromethane, dried with NaOH (10 pellets~0.8 grams), filtered, and cooled in an ice bath. A solution of 3-chloroperbenzoic acid (MCPBA) (57%, 30.3 g, 0.1 mol) in 150 mL of dichloromethane was added dropwise. A white precipitate formed upon addition of MCPBA and dissolved after stirring for a while. After complete addition of MCPBA, the reaction was allowed to warm to room temperature and was stirred overnight. The resulting clear yellow solution was washed with water (1×), dilute sodium hydroxide (2×), 5% hydrochloric acid (2×), water (2×) and dried over MgSO$_4$. The dichloromethane solvent was then stripped, leaving colorless liquid. TLC showed the presence of benzaldehyde in the liquid. Acetonitrile (150 mL) was added to the liquid and the solution was refluxed overnight. The acetonitrile solvent was then stripped, leaving colorless liquid. The nitrone product was purified on a silica gel column, eluting with hexane/EtOAc (2:1) to obtain 0.54 g of the title compound as a pale yellow solid, m.p. 73–75° C.

Example 4

Synthesis of α-(4-Benzyloxyphenyl)-N-tert-butylnitrone

A mixture of 4-benzyloxybenzaldehyde, N-tert-butylhydroxylamine and catalytic amount of p-toluenesulfonic acid monohydrate in benzene was refluxed under argon atmosphere with a Dean-Stark trap to remove generated water. The mixture was then rotary evaporated to give a residue which was purified by recrystallization. The title compound was obtained in 89.3% yield as a white powder, m.p. 11.0° C. (R$_f$=0.66 on a silica gel plate using EtOAc as an eluant).

Spectroscopic data were as follows:

IR (KBr, cm$^{-1}$): 2982 (CH), 1601 (C=N & benzene ring), 1508 (benzene ring), 1242 (Ar—O), 1170 (N—O). and 1005 (benzyl-O)

$^1$H NMR (CDCl$_3$, 270 MHZ): δ=8.29 (2H, d, J=9.2 Hz, aromatic 2H), 7.46 (1H, s, CH=N), 7.41–7.31 (5H, m, aromatic 5H), 7.00 (2H, d, J=9.2 Hz, aromatic 2H), 5.10 (2H, s, OCH$_2$), and 1.60 (9H, s, 3 CH$_3$) ppm.

$^{13}$C NMR (CDCl$_3$, 67.9 MHZ): δ=159.89, 136.47, 130.64, 129.35, 128.52, 128.00, 127.42, 124.23, 114.58, 70.05, 69.91 and 28.25 ppm

Example 5

Synthesis of N-Benzyl-α-(4-acetamidophenyl)nitrone

Using 4-acetamidobenzaldehyde and N-benzylhydroxylamine (prepared from the hydrochloride salt by treatment with K$_2$CO$_3$) and following the procedures described herein, the title compound was prepared as a yellow powder, m.p. 230.7–237.7° C.

Example 6

Synthesis of α-(2-Ethoxyphenyl)-N-cyclopentylnitrone

Using 2-ethoxybenzaldehyde and N-cyclopentylhydroxylamine and following the procedures described herein, the title compound was obtained in 72.6% yield as white crystals, m.p. 87.3° C. (R$_f$=0.43 on a silica gel plate using hexanes:EtOAc, 2: 1, v:v, as an eluant).

Spectroscopic data were as follows:

IR (KBr, cm$^{-1}$): 2976 (CH), 2957 (CH), 1636 (C=N), 1597 & 1564 benzene ring), 1251 (Ar—O), 1165 (N—O). and 1043 (Et-O).

$^1$H NMR (CDCl$_3$, 270 MHZ): δ=9.33 (1H, dd, J=7.8 & 1.7 Hz, aromatic 1H), 7.98 (1H, s, CH=N), 7.32 (1H, ddd, J=8.2, 7.5 & 1.7 Hz, aromatic 1H), 6.99 (1H, td, J=6.1 & 7.8 Hz, CH), 4.07 (2H, q, J=7.0 Hz, OCH$_2$), 2.35–2.22 (2H, m, cyclopentyl 2H), 2.07–1.88 (4H, m, cyclopentyl 4H), 1.72–1.57 (2H, m, cyclopentyl 2H) and 1.45 (3H, t, J=7.0 Hz, CH$_3$) ppm.

$^{13}$C NMR (CDCl$_3$, 67.9 MHZ): δ=156.11, 131.00, 128.64, 127.31, 120.50, 119.88, 110.57, 76.64, 63.85, 31.38, 25.55 and 14.74 ppm.

Example 7

Synthesis of α-(4-Acetoxy-3,5-di-tert-butylphenyl)-N-tert-butylnitrone

4-Acetoxy-3,5-di-tert-butylbenzaldehyde (113.16 g, 0.41 mol) was placed in a 2 L round-bottomed flask fitted with a magnetic stirrer. Benzene (500 mL) was added and the mixture was stirred until the solids dissolved. To the resulting red solution was added tert-butylhydroxylamine (43.80 g, 0.49 mol) and silica gel (20 g). The mixture was refluxed overnight at which time TLC showed no remaining starting material (R$_f$=0.31 for product and 0.80 for starting material using 3:1 hexanes/EtOAc). The benzene was removed in vacuo on a rotovap to provide a grey solid. The solid was dissolved in a minimum amount of ethyl acetate and the flask was left to stand in the freezer. The white crystals which formed were separated, washed with hexanes and dried under vacuum to afford 105.78 g of the title compound as a crystalline white solid (74.4% yield), m.p. 227.0–248.9° C.

Spectroscopic data were as follows:

$^1$H NMR (CDCl$_3$, 270 MHz): δ=8.32 (1H, s, phenyl H), 7.50 (1H, s, nitronyl H). 2.35 (3H, s, 1 CH$_3$), 1.61 (9H, s, 3 CH$_3$), 1.37, s, 18 CH$_3$).

$^{13}$C NMR (CDCl$_3$, 270 MHz): δ=170.7, 149.2, 142.6, 129.7, 128.4, 127.2, 70.7, 35.5, 31.4, 28.5, 22.6.

Example 8

Synthesis of N-tert-butyl-α-(4-aminosulfonylphenyl)nitrone

Using 4-aminosulfonylbenzaldehyde and N-tert-butylhydroxylamine and following the procedures described herein, the title compound was prepared as a white powder, m.p. 219.1–219.4° C.

Spectroscopic data were as follows:

$^1$H NMR (CDCl$_3$, 270 MHz): δ=8.32 (1H, s, phenyl H), 7.50 (1H, s, nitronyl H). 2.35 (3H, s, 1 CH$_3$), 1.61 (9H, s, 3 CH$_3$), 1.37 (s, 18 CH$_3$).

Example 9

Synthesis of α-(2-Ethoxyphenyl)-N-cyclobutylnitrone

2-Ethoxybenzaldehyde was combined with cyclobutylamine hydrochloride in chloroform and the solution was refluxed for 22 hours. Upon completion of the reaction, the solution was cooled to room temperature and concentrated under vacuum to give an oily residue, which was N-cyclobutyl-(2-ethoxy)phenyl imine.

The oily residue was dissolved in ethanol and the solution was cooled with an ice bath. Sodium borohydride was added in portions and the reaction mixture was stirred at ambient temperature for 21 hours. The solution was then concentrated under vacuum and the residue was suspended in dichloromethane. A precipitate formed which was filtered. The filtrate was concentrated to give a liquid, which was passed through a silica gel filled funnel (eluting with hexane/ethyl acetate, 2:1) to afford N-cyclobutyl-(2-ethoxy)phenylamine.

The N-cyclobutyl-(2-ethoxy)phenylamine was suspended in propanone and mixed with sodium tungstate dissolved in water. The mixture was cooled with an ice bath and hydrogen peroxide was added dropwise with continuous stirring. The mixture was stirred for 19 hours. The solution was then concentrated under vacuum and the residue suspended in dichloromethane. The mixture was filtered and the filtrate evaporated. The residue was purified by dry flash column chromatography and then recrystallized from hexane to give the title compound as a cream-colored solid, m.p. 76.0° C. (9.4% yield).

Spectroscopic data were as follows:

$^1$H NMR (CDCl$_3$, 270 MHz): δ=9.31 (1H, dd, J=7.7, 1.7), 7.87 (1H, ddd, J=8.2, 7.7, 1.7). 6.99 (1H, td, J=7.7, 0.7), 6.84 (1H, dd, J=8.2,0.7), 4.59 (1H, quin. J=8.1), 2.82 (2H, m), 236 (2H, m), 1.92 (2H, m), 1.43 (23H, t, J=7.0).

Bioassay Example 1

Evaluation of Compounds in TNBS Model for IBD

In this experiment, the ability of compounds of this invention to reduce colonic inflammation is demonstrated using the trinitrobenzene sulphonic acid ("TNBS") model for IBD. The TNBS model is one of the standard IBD models used in IBD discovery research and it has been extensively evaluated in rodents. See, for example, C. O. Elson et al. (1995), Experimental Models of Inflammatory Bowel Disease, *Gastroenterology*, 109: 1344–1367 and references cited therein. In this model, a single enema of TNBS induces a prolonged colonic inflammatory response (up to several weeks) that is transmural and is accompanied by oxidative damage as evidenced by an increase in myeloperoxidase ("MPO") activity. Additionally, the inflammation is characterized by discrete areas of acute necrosis, inflammation and muscle thickening. Agents with anti-inflammatory effects in patients with IBD show efficacy in this model. Although the mechanism by which TNBS induces an inflammatory response is unknown, it is thought to have an immunological basis.

Induction of Colitis

Male Sprague-Dawley rats (200–250 g) were housed in standard cages (2 per cage) and fed rat chow and tap water ad libitum. After an overnight fast, rats were brought into the laboratory and randomized into treatment groups. Colitis was induced by intrarectal administration of 0.5 ml of TNBS solution (50 mg/kg in 50% ethanol) using a 1 mL syringe attached to a 5 cm polyethylene catheter. Control animals received saline (0.9%) or a 1% methyl cellulose suspension at identical time points.

Tissue Analysis

Three days after TNBS administration, the rats were sacrificed and the colons excised and opened longitudinally. In 5 cm segments of colon, gross morphology was determined using the following scale:

| Grade | Finding |
| --- | --- |
| 0 | No damage |
| 1 | One area of Inflammation (red), no ulcers |
| 2 | Ulcers, no area of inflammation |

-continued

| Grade | Finding |
|---|---|
| 3 | Ulcers, one area of inflammation |
| 4 | More than 2 ulcers, inflammation at one site |
| 5 | More than 2 ulcers, inflammation >1 cm |

The weights of each 5 cm colonic segment were also recorded to assess inflammatory induced edema.

Dosing Regimen

Each of the compounds from Examples 1–6 were tested in the TNBS model at 10 mg/kg p.o. (oral) dosing. Each of the test compounds was administered by oral gavage as a 1% carboxy methyl cellulose ("CMC") suspension 1 hour prior to the administration of TNBS. Control rats were given CMC only.

Results

Each of the test compounds reduced TNBS-induced damage compared to the controls. The reduction in TNBS-induced damage ranged from about 25% to about 60% (average scores).

Bioassay Example 2

Mouse Dextran Sulfate IBD Model

Another model used for screening candidate IBD-treating compounds is the Dextran Sulfate ("DSS") model. Similar to the TNBS model, DSS induced colitis is widely used as a screening tool for IBD therapeutics. When administered orally, DSS induces IBD-like symptoms in Swiss-Webster mice. This model can be used to determine the effectiveness of compounds of this invention when such compounds are administered orally (p.o.).

Individually housed 30–40 g male Swiss-Webster mice (B & K Universal, Fremont, Calif.) receive 3% DSS (Sigma Chemicals, St. Louis, Mo.) in their drinking water for 7 days. All animals receive food and water ad libitum.

Two groups of mice are dosed orally with either the test compound in a dosing vehicle (1% methyl cellulose, dose range of 10 mg/kg to 30 mg/kg) or dosing vehicle alone (control).

Clinical signs of colitis are assessed by a disease activity index ("DAI") consisting of changes in stool characteristics, fecal occult bleeding and body weight loss. The DAI is very similar to the Crohn's Disease Activity Index used in clinical trials to evaluate new agents to prevent/treat IBD. The DAI data are analyzed using ProcAnova in SAS with a Bonferoni post-hoc analysis, and Model 108 in WinNonlin™ (Professional Version 1.5, Scientific Consulting, Apex, N.C.) for the $ED_{50}$ and $E_{max}$ values. The wet weight and myeloperoxidase ("MPO") data (collected only on Day 7) are analyzed by Proc TTest in SAS. MPO is a marker for neutrophil infiltration. The following criteria are employed in this assay:

DAI Scoring (Daily)

Stool Characteristic: 0=normal, 2=loose and 4=diarrhea

Fecal Occult Blood: 0=negative, 2=positive, 4=gross bleeding

Weight Change: 0=0–1%, 1=1 to <5%, 2=5% to <10%, 3=10 to <20%, 4=>20%

MPO (Day 7 Only)

Two strips of colonic tissue/mouse

MPO activity by spectrophotometric assay

Bioassay Example 3

Establishment of the Dose-Response Characteristics in the Mouse Dextran Sulfate Model To determine the dose-response relationship of a test compound in the DSS Mouse Model, the following procedure is used.

Experimental conditions and statistical analyses are the same as the Mouse Dextran Sulfate IBD Model, except four groups of mice (n=8–10/group) are used. Animals are dosed orally with either test compound (3, 10 or 30 mg/kg) or vehicle alone. In addition, the following procedure is introduced to evaluate the histology in the animals:

Histology Score

5–6 slices/segment with 15–18 total pieces/colon

Score for extent of damage: 0=1–25% involvement, 1=26–50% involvement, 2=51–75% involvement, 3=76–100% involvement Score for grade:

0=intact crypt, 1=loss of ⅓ crypt, 2=loss of ⅔ crypt, 3=loss of entire crypt with surface epithelium intact, 4=loss of entire crypt and erosion of surface epithelium Score for Severity:

0=normal, 1=focal inflammatory cell infiltrate including PMNs, 2=inflammatory cell infiltration, gland dropout and crypt abscess, 3=mucosal ulceration Single, evaluator (qualified pathologist) blinded to the treatment conditions.

Bioassay Example 4

Effect of Test Compounds on Flux of Reactive Oxygen Species Induced by TNF-α

Oxidative stress agents (OSA) are thought to be involved in cell death in IBD and are key initiator in the cascade of events leading to apoptosis. The purpose of this study is to evaluate the effect of a test compound on cytokine-induced OSA flux.

To visualize OSA, the dye dihydrodichlorofluorescein diacetate is used. This non-fluorescent dye is taken up by cells and deacetylated to its non-fluorescent congener dihydroclichlorofluorescein ($H_2DCF$), which is trapped within cells. Reactive oxygen species ("ROS") react with $H_2DCF$, converting it to the highly fluorescent DCF. DCF fluorescence can be measured spectrofluorometrically and can also be visualized in intact cells using fluorescent microscopy.

SK-N-MC cells (American Type Culture Collection, Rockville, Md.) are plated at 250,000 cells/well in 24-well Corning plates. Following plating, the cells are maintained in retinoic acid medium (5 $\mu$M) for five days and then treated with a test compound at 100 $\mu$M for 1 hour prior to TNF-α (3.0 ng/mL) treatment. TNF-α and $H_2DCF$ are added simultaneously and cultures are incubated for an additional 4 hours. Following incubation, cultures are read in a cytofluorometer at 485–530 nm wavelength to detect increased DCF formation. Relative fluorescence units (RFU) values for the respective treatment conditions are compared. In this assay, higher fluorescence readings indicate ROS production. Thus, reductions in fluorescence indicates reduction in ROS production.

Bioassay Example 5

Effect of Compound A on TNF-α Induced Apoptosis in a Human Cell Model

This test is used to evaluate the potential of a test compound to prevent TNF-α induced apoptosis.

A test compound is evaluated in an in vitro model of TNF-α induced toxicity (see Pulliam et al. *J. Neurosci. Res.* 21:521–530 (1998)). In this model, human brain cell aggregates from fetal tissue are treated with TNF-α which caused an apoptotic cell death. Brain cell aggregates prepared from 1 brain were incubated for 10–12 days before experimentation. Aggregates are weighed out (100 mg/flask) and aliquoted into 10 mL flasks. TNF-α is used at a concentration of 1 ng. The test compound is added 1 hour prior to the TNF-α. Experiments include untreated brain aggregates, TNF-α-treated brain aggregates, TNF-α-+test compound treated aggregates and test compound treated aggregates. After TNF-α is added, aggregates are incubated for an additional 48 h. After this time, brain aggregates are centrifuged for 5 min at 500 rpm. The supernatant is removed and the pellet is lysed for determination of programmed cell death. (Boeringer Mannheim Cell Death Kit ELISA).

Bioassay Example 6

Effect of Test Compound on TNF-α Induced Reduction in bcl-2

Cytokine-mediated apoptosis or programmed cell death is believed to be involved in a number of diseases including IBD. Reductions in bcl-2 are a major signal in initiation of the apoptotic cascade (see Jourd'heuil et al., J. Clin Gastroenterol. 25(Suppl):S61–S72 (1997)). The purpose of this study is to investigate the effects of a test compound on bcl-2 protein levels in a cellular model of cytokine mediated apoptosis.

SK-N-MC cells (American Type Culture Collection, Rockville, Md.) are plated at 500,000 cells/plate and treated with retinoic acid ("RA") (5 μM) for 5 days. Following RA treatment, the cells are incubated with a test compound (100 μM) for 1 hour. Cells are then treated with increasing concentrations of TNF-α (0, 0.3 and 3 ng/mL) for 6 h. The cells are harvested and lysed and bcl-2 is measured in the lysate using an ELISA assay (Boehringer Manheim). Quantification of bcl-2 is based on a standard curve and results are expressed as units/mL of bcl-2 in the sample.

What is claimed is:

1. A pharmaceutical composition for the treatment or prophylaxis of inflammatory bowel disease comprising a pharmaceutically acceptable carrier and an effective inflammatory bowel disease-treating amount of a compound selected from the group consisting of:

N-tert-butyl-α-(3,5-di-tert-butyl-2-hydroxyphenyl)nitrone,
N-isobutyl-α-phenylnitrone,
N-benzyl-α-(4-acetamidophenyl)nitrone,
N-tert-butyl-α-(1-methylindol-3-yl)nitrone,
N-tert-butyl-α-(3,5-di-tert-butyl-4-acetoxy)nitrone,
N-tert-butyl-α-(4-aminosulfonylphenyl)nitrone,
and pharmaceutically acceptable salts thereof.

2. A pharmaceutical composition for the treatment or prophylaxis of inflammatory bowel disease comprising a pharmaceutically acceptable carrier and an effective inflammatory bowel disease-treating amount of N-tert-butyl-α-(3,5-di-tert-butyl-2-hydroxyphenyl)nitrone and pharmaceutically acceptable salts thereof.

3. The pharmaceutical composition of claim 1 wherein the compound is N-isobutyl-α-phenylnitrone and pharmaceutically acceptable salts thereof.

4. A pharmaceutical composition for the treatment or prophylaxis of inflammatory bowel disease comprising a pharmaceutically acceptable carrier and an effective inflammatory bowel disease-treating amount of N-benzyl-α-(4-acetamidophenyl)nitrone and pharmaceutically acceptable salts thereof.

5. A compound selected from the group consisting of:
N-isobutyl-α-phenylnitrone,
N-benzyl-α-(4-acetamidophenyl)nitrone,
N-tert-butyl-α-(1-methylindol-3-yl)nitrone,
N-tert-butyl-α-(4-aminosulfonylphenyl)nitrone,
and pharmaceutically acceptable salts thereof.

* * * * *